United States Patent [19]
Kim et al.

[11] Patent Number: 6,159,451
[45] Date of Patent: Dec. 12, 2000

[54] MANUFACTURING PROCESS OF GLUCOSYLTRANSFERASE INHIBITORS FROM CACAO BEAN HUSK

[75] Inventors: Dong Young Kim, Kyungki-do; Hyen Joo Park, Seoul; Hyung Hwan Park; Han Soo Kim, both of Kyungki-do; Ik Boo Kwon, Seoul, all of Rep. of Korea

[73] Assignee: Lotte Confectionery Co., Ltd., Rep. of Korea

[21] Appl. No.: 09/352,821

[22] Filed: Jul. 13, 1999

[30] Foreign Application Priority Data

Jun. 30, 1999 [KR] Rep. of Korea ............... 99-25998

[51] Int. Cl.[7] ............... A61K 7/26; A61K 35/78; A23L 1/30; A61L 9/01
[52] U.S. Cl. ............... 424/58; 424/195.1; 424/49
[58] Field of Search ............... 424/49–58, 195.1

[56] References Cited

U.S. PATENT DOCUMENTS

| | | | |
|---|---|---|---|
| 4,156,030 | 5/1979 | Eggon | 426/540 |
| 4,322,444 | 3/1982 | Zuilichem et al. | 426/241 |
| 4,532,147 | 7/1985 | Jonas et al. | 426/655 |
| 4,908,212 | 3/1990 | Kwon et al. | 424/448 |

OTHER PUBLICATIONS

Patent Cooperation Treaty (PCT) International Search Report, mailed Apr. 4, 2000, for file No. PCT/KR99/00616.
Gryuner et al 8 Caplus 23914 (1972) Prikl. Biokhim. Mikrobio 67(4):398–403, 1971.
Takizawa et al 8 Caplus 336 884 J. Nutr:Sci. Vitaminol–44(2):313–321 (1998).
Sonbongi et al. 8 Caplus 6624 J.Agric. Food.Chem. 46(2): 454–457(1998).
Porter et al 8 Caplus 47015 (1991) Phytochemistry 30(5): 1657–1663, 1991.
Kharlamova 8 Capus 487294 (1970) Ref. 2H. Khim Abstr. 11R 135, 1971
An et al 8 Caplus 454925 (1994) Hanguk Nonghwa Hakhochi 37(6):498–502, 1995.
Osawa et al 8 Caplus 626897 (1990) Bull. Tokyo Dent. Co:l 31(2):125–128, (1990).
Sugiyama et al 8 Caplus 552425 (1989) JP 0112965 (May 11, 1989).
Kimura et al 8 Caplus 524920 (1973) JP 54 01 0567, 1973.
Salmonowicz et al 8 Caplus 454675 (1970) Tluszcze Jadalne 14(1):7–18, 1970.
"Preventive Effect of Green Tea Polyphenols against Dental Caries in Conventional Rats", *Biosience, Biotechnology, and Biochemistry*, by Senji Sakanaka, et al., 56 (4), pp. 592–594, 1992.
"Dietary Antioxidant Flavonoids and Risk of Coronary Heart Disease: the Zutphen Elderly Study", *The Lancet*, by Michael G. L. Hertog, et al., vol. 342, No. 8878, Saturday Oct. 23, 1993.
"Resolution of Streptococcus Mutans Glucosyltranferases into Two Components Essential to Water–Insoluble Glucan Synthesis", *FEBS Letters*, by Kazuo Fukushima, et al., vol. 128, No. 2, pp. 213–216, Jun. 1981.
"The Contribution of Plant Food Antioxidants to Human Health", *Trends in Food Science & Technology*, Mar. 1995, vol. 6, pp. 75–82.
"Effects of Chinese Green Tea and Oolong Tea on Blood Pressure, Plasma and Liver Lipids in Spontaneously Hypertensive Rats and Rats with Fructose–Induced Hyperlipidemia", *Jpn. Soc. Nutr. Food Sci.*, by K. Iwata, et al., vol. 40, No. 6, pp. 469–477, 1987.

*Primary Examiner*—Shep K. Rose
*Attorney, Agent, or Firm*—Finnegan, Henderson, Farabow, Garrett & Dunner, L.L.P.

[57] ABSTRACT

This invention relates to a process for manufacturing a fraction of cacao bean husk having an inhibitory activity against glucosyltransferase in the prevention of tooth decay and more particularly, to the process for manufacturing a fraction of cacao bean husk having more potent activity against glucosyltransferase in the prevention of tooth decay, while providing an economically feasible recovery process designed to treat enormous wastes of cacao bean husk, wherein it comprises the steps in which:

an extract of cacao bean husk, which has already proven to exhibit an excellent inhibitory activity against glucosyltransferase, is formed from cacao bean husk; and, the extract is again added to an adsorption resin and fractioned by 50% thanol aqueous solution.

5 Claims, No Drawings

MANUFACTURING PROCESS OF GLUCOSYLTRANSFERASE INHIBITORS FROM CACAO BEAN HUSK

BACKGROUND OF THE INVENTION

Field of the Invention

This invention relates to a process for manufacturing a fraction of cacao bean husk having an inhibitory activity against glucosyltransferase in the prevention of tooth decay and more particularly, to the process for manufacturing a fraction of cacao bean husk having more potent activity against glucosyltransferase in the prevention of tooth decay, while providing an economically feasible recovery process designed to treat enormous wastes of cacao bean husk, wherein it comprises the steps in which:

an extract of cacao bean husk, which has already proven to exhibit an excellent inhibitory activity against glucosyltransferase, is formed from cacao bean husk; and, the extract is again added to an adsorption resin and fractioned by 50% ethanol aqueous solution.

DESCRIPTION OF THE RELATED ART

Cacao (Theobroma cacao L.), an active ingredient of chocolate and cocoa, denotes a mysterious meaning of God's food. The country of origin for cacao is said to be some areas ranging from Central America to the northern parts of South America. Several countries in Central America have regarded cacao as one of the valuable foods including corn, which had been long cultivated from the prehistoric times. It was said that Aztec leaders, who inhabited in the Central America during 13~16 centuries, would take a roasted cacao bean, mixed with some spices, as a tonic. Thereafter, cocoa was widely distributed through the whole regions of Europe and a solid chocolate was invented by a young person in Switzerland for the first time in the world. Such first introduction of chocolate has contributed much to drastic production increase of cacao bean. Currently, chocolate is the most popular favorite food, which is beloved by all people around the world.

Cacao bean, an active ingredient of chocolate, commonly contains a large amount of edible fibers and polyphenols, even though its composition is somewhat different depending on the country of origin. These polyphenols having a larger portion in green tea has been reported to have various biological activities in the body; for example, a tooth decay prevention action [Sakanaka, S., et al., Biosci & Biochem., 56, 592,1992], antihypertensive actions [Iwata, K., et al., Jpn. Soc. Nutr. Food Sci., 40, 469, 1987], cardiovascular action [Hertog, M.G.L., et al., Lancet, 342, 1007, 1993] and antioxidative action [Ramaretnam, N., et al., Trends in Food Sci. Technol., 6, 75, 1945]. Recently, through intensive studies to extract these polyphenols from some plants containing a large amount of these polyphenols such as green tea, oolong tea, apple and grape, they are being widely used as raw materials of functional foods, cosmetics and pharmaceuticals.

Meantime, during the manufacturing process of chocolate, the nib portion of peeled-off cacao bean is used as an raw material of chocolate or cocoa, while a majority of its husks (about 15 wt % to the total weight of cacao bean), as a by-product, is abandoned. More specifically, the current worldwide production output of cacao bean accounts for about 2.5 million tons, while about 400,000 tons of cacao bean husk are being discharged. According to the annual trade statistics released by the Korea's Office of Customs Administration in 1990, about 600 tons of cacao bean husk have been abandoned as wastes in Korea. Nevertheless, since the cacao bean husk contains larger amount of cellulose and polyphenols than nib, more researches have focused on the methods of re-utilizing the cacao bean husk as a natural resource.

In view of the fact that these polyphenols extracted conventionally from the green tea and oolong tea are quite expensive and their inhibition activities against glucosyltransferase are relatively low due to their monomer composition containing catechin or epicacatechin, the re-utilization for the cacao bean husk is under active development.

To this end, the inventor et al. have noted that cacao bean husk obtained from the manufacture of chocolate as by-product is economically feasible and its chemical polymer composition containing procyanidin A and procyanidin C-1 is effective in the inhibition of glucosyltransferase, a major cause of tooth decay. Thus, the inventor et al. has already prepared a chewing gum designed to prevent tooth decay by blending a soluble extract of cacao bean husk [Korea Patent No. 45179, 1991: U.S. Pat. No. 4,908,212, 1990].

However, the conventional extract of cacao bean husk has been recognized some disadvantage in actual application in that its $IC_{50}$ value (50% inhibitory concentration against enzyme activity) is above 80 $\mu$g/ml compared with an extract of oolong tea (Suntory of Japan) having the $IC_{50}$ value of 40 $\mu$g/ml, as an excellent glucosyltransferase inhibitor in the market, thus representing less inhibitory activity against glucosyltransferase.

Under such circumstances, there is urgent need for the development of a novel method to prepare a fraction of cacao bean husk with more potent inhibitory activity against glucosyltransferase.

SUMMARY OF THE INVENTION

To manufacture an extract of cacao bean husk having more potent inhibitory activity against glucosyltransferase, various reaction conditions have been carefully studied such as selection of appropriate solvents, extraction conditions and separation process of active substances. Thus, this invention is brought to perfection by finding the optimum conditions to enhance the inhibitory activity against glucosyltransferase.

Therefore, an object of this invention is to provide a process for manufacturing a fraction of cacao bean husk having more potent activity against glucosyltransferase in the prevention of tooth decay, together with an economically feasible recovery process designed to treat enormous wastes of cacao bean husk.

DETAILED DESCRIPTION OF THE INVENTION

This invention is characterized by a process for manufacturing a fraction of cacao bean husk having more potent activity against glucosyltransferase in the prevention of tooth decay, wherein it comprises the steps in which:

4~10 weight parts of 50% acetone aqueous solution are added to 1 weight part of dried cacao bean husk, stirred under reflux at 40~80° C. for 4~6 hours, and extracted two times to give an extract of cacao bean husk having more potent activity against glucosyltransferase;

the extract of cacao bean husk, so formed, is added to styrene-based adsorption resin, washed with 1~2 weight parts of 20% ethanol, followed by the addition of 1~2 weight parts of 50% ethanol for fractionation; and, the extract is concentrated under reduced pressure at 40~50° C.

Further, this invention is characterized by the fraction of cacao bean husk having a tooth decay prevention function based on the above mentioned process.

This invention is explained in more detail as set forth hereunder.

This invention relates to a process for manufacturing a fraction of cacao bean husk having an inhibitory activity against glucosyltransferase in the prevention of tooth decay and more particularly, to the process for manufacturing a fraction of cacao bean husk having more potent inhibitory activity against glucosyltransferase in the prevention of tooth decay, wherein it comprises the steps in which:

an extract of cacao bean husk, which has already proven to exhibit an excellent inhibitory activity against glucosyltransferase, is formed from cacao bean husk; and, the extract is again added to an adsorption resin and fractioned by 50% ethanol aqueous solution.

According to this invention, the process for manufacturing an extract of cacao bean husk is explained in more detail as set forth hereunder.

First, among cacao bean husk which are discharged in the process of manufacturung chocolate or cocoa drinks, the husks with less than 2 mm in average size are carefully selected. Then, 4~10 weight parts of 50% acetone aqueous solution as solvent are added to 1 weight part of dried cacao bean husk, stirred under reflux at 40~80° C. for 4~6 hours and extracted. The extract is filtered off(or centrifugation), concentrated with a vacuum evaporator and dried under vacuum. The above procedure is repeatedly performed two times to obtain an extract of cacao bean husk.

Hence, the reason why 50% acetone aqueous solution is employed as solvent lies in the fact that unlike other solvents (e.g., hot water, methanol aqueous solution, 100% ethanol, methanol aqueous solution, 100% methanol or 100% acetone), an extract, which is prepared in the presence of 50% acetone aqueous solution, exhibits the most excellent inhibitory activity against glucosyltransferase and also effective in extracting all water-soluble and fat-soluble substances, since it can react with all of hydrophilic and hydrophobic materials. Meantime, if less than 4 weight parts of the solvent are added to 1 weight part of cacao bean husk, any stable yield of extract and its desired inhibitory activity against glucosyltransferase cannot be ensured but in case of exceeding 10 weight parts of cacao bean husk, the cost increase during extraction is disadvantageous economically and industrially. Further, if the extraction process is performed at the temperature of more than 40° C., the inhibition rate against glucosyltransferase becomes high but in case of exceeding 80° C., the extraction yield become decreasing on the contrary with the possible heat-denatured raw materials. Further, if the extraction process is performed for less than 4 hours, any stable yield of extract and its desired inhibitory activity against glucosyltransferase cannot be ensured.

When the reaction mixture is stirred, its extraction yield and inhibitory activity against enzyme is simultaneously increased.

In addition, the reason why the process is repeated two times is that when the first extract is mixed with the second extract, the most excellent inhibition activity against glucosyltransferase is obtained.

When the inhibition activity of an extract against glucosyltransferase, so prepared from the above process, is compared, the extract of cacao bean husk according to the Korea Patent No. 45179 has an $IC_{50}$ of about 80 μg/ml, while an extract of oolong tea (Suntory of Japan), which is currently marketed as an excellent glucosyltransferase inhibitor, has an $IC_{50}$ of 40 μg/ml. This emphasizes the need to develop a new method of manufacturing an extract with more potent inhibitory activity against enzyme.

According to this invention, therefore, the extract of cacao bean husk, so obtained, is added to styrene-based adsorption resin which serves to adsorb some organic compounds of high molecular weight, washed with 20% ethanol and fractioned again in 50% ethanol aqueous solution under appropriate conditions to obtain the fraction of cacao bean husk with tooth decay prevention function. This procedure is explained in more detail as set forth hereunder.

The most distinctive feature of this invention is that the extract of cacao bean husk, so obtained, is added to a column with the styrene-based adsorption resin, since the resin functions as an adsorbent to combine with some glucosyltransferase-inhibitory materials only and then the concentrated materials with tooth decay prevention function can contribute much to more potent inhibitory activity against glucosyltransferase.

The extract of cacao bean husk, so formed, is added to styrene-based adsorption resin, washed with 1~2 weight parts of 20% ethanol, followed by the addition of 1~2 weight parts of 50% ethanol for fractionation; and, the fraction is concentrated under reduced pressure at 40~50° C. to obtain a fraction of cacao bean husk having a tooth decay prevention function. Hence, when the extract is fractioned by 50% ethanol aqueous solution, its inhibitory rate against enzyme is the most high. If less than 1 weight part of the fraction solvent is added, all of the active ingredients cannot be eluted but in case of exceeding 2 weight parts, the production cost becomes increasing. Further, when the extract is fractioned by solvent, its elution flow rate is 10~100 ml/min. If the elution flow rate exceeds 100 ml/min, the yield of final product is decreased due to the insufficient adsorption time. However, if the elution flow rate is less than 10 ml/min, the prolonged adsorption time makes the fraction uneconomical.

From the fraction of cacao bean husk, so obtained from the adsorption column chromatography, the fraction washed with 20% ethanol shows little inhibitory activity against glucosyltransferase compared with the extract of cacao bean husk, while the fraction eluted with 50% ethanol has $IC_{50}$ of less than 20 μg/ml, thus reflecting that its inhibition rate against glucosyltransferase is increased more than two times.

Therefore, a fraction of cacao bean husk of this invention can have better inhibitory activity against glucosyltransferase as well as economically efficient recycling effects to treat enormous amounts of cacao bean husk.

The fraction of cacao bean husk, so prepared according to this invention, can has more potent activity against glucosyltransferase in the prevention of tooth decay, while providing an economically feasible recovery process designed to treat enormous wastes of cacao bean husk The following specific examples are intended to be illustrative of the invention and should not be construed as limiting the scope of the invention.

MANUFACTURING EXAMPLE

Preparation of Glucosyltransferase

Glucosyltransferase derived from Streptococcus mutans, a major strain involved in tooth decay, was prepared by a slightly modified method of Fukushima et al. [Fukushima, K. and Motoda, R., FEBS Lett., 128(2), 213, 1981]. S. mutans ATCC 6715, a representative production strain of glucosyltransferase, was cultivated at 37C for 24 hours. Then, 2 volume % of the seed culture broth was inoculated into a 4.5 L brain-heart infusion medium to perform the incubation under the same conditions. The incubation was completed, the culture broth was centrifuged at 6,000 rpm at room temperature for 20 minutes. 3 L of ethanol, previously cooled, was added to the supernatant to precipitate proteins, left at 4° C. overnight. Then, the residue was centrifuged again at 8,000 rpm for 30 minutes to obtain a precipitate. Then, the precipitate was re-suspended in 10 ml of 0.05M phosphate-buffered solution (pH 6.8) to make it as a crude enzyme solution and stored in a freezer at −20° C. An appropriate amount of the crude enzyme solution diluted in 0.05M phosphate-buffered solution (pH 6.5) was used for each test, if deemed necessary.

REFERENCE EXAMPLE 1

Tests for Selecting Optimum Extraction Solvents 300 ml of solvent, as described in the following table 1, was added to 30 g of completely dried cacao bean husk (less than 2 mm in size), stirred at 60 rpm at 60° C. and extracted under reflux for 4 hours. After the extraction was completed, the solution was filtered off to collect the extraction solution only. Then, the same amount of 50% ethanol aqueous solution was added to the residue to perform the same extraction process repeatedly. The extraction solution, so obtained, is mixed with the previously extracted solution, and concentrated by vacuum evaporator at 50° C. to obtain an extract of cacao bean husk.

Further, tests for detecting the inhibitory activities of each extract, so obtained, against glucosyltransferase as well as for detecting polyphenol contents of each extract was performed in the following test methods, as shown in the following table 1.

Test Methods

1) Detection of the Inhibitory Activities of Each Extract Against Glucosyltransferase:

0.8 ml of substrate solution consisting of 12.5 g of sugar and 0.25 g of sodium azide dissolved in 1L of a 62.5 mM phosphate-buffered solution (pH 6.5), 0.025 ml of glucosyltransferase solution, so prepared from the manufacturing example and 0.175 ml of each sample was put into a test tube (length: 100 mm, inner diameter: 13 mm) to make a final volume of 1 ml. Hence, control was same as those used in the above testing method, but a same amount of distilled water was added instead of each extract. After the test tube was given a slope of about 30 degrees, the reaction was performed at 37° C. for 16 hours. After the reaction was completed, the supernatant contained in the test tube was quietly decanted. After residual glucan was dispersed by using an ultrasonicator for 5 seconds following the addition of 3 ml of distilled water, the absorbance at 550 mm was measured with an UV-visible spectrophotometer (UV-260, Shimadzu Co., Japan) to detect the inhibitory activities of each extract against glucosyltransferase based on the following equation 1:

Inhibition rate (%)=(A−B) over (A)×100    Equation 1

Where, A is an absorbance of control; B is an absorbance of extract-added group.

2) Detection of Polyphenol Contents of Each Extract:

The polyphenol contents of each sample were measured by a slightly modified method of AOAC. First, 750 µl of distilled water was put into Eppendorf tube, followed by the addition of 100 µl of sample solution dissolved at an appropriate concentration. Then, a mixture of 50 µl of Folin Denis reagent and 100 µl of saturated sodium carbonate solution was added to the reaction mixture, blended well with a vortex mixer and reacted at room temperature for 1 hour. After the reaction was completed, the absorbance at 725 mm was measured to determine the polyphenol contents in comparison with the previously prepared standard curve. Hence, the standard curve was prepared using epicatechin as standard according to common method.

TABLE 1

| Solvent | Yield (%) | Inhibitory activity against Gtase $IC_{50}$ (µg/ml) | Contents of polyphenol (%) |
|---|---|---|---|
| Methanol | 8 | 100< | 8 |
| Ethanol | 9 | 100< | 8 |
| Acetone | 11 | 100< | 7 |
| 50% methanol | 17 | 100< | 14 |
| 50% ethanol | 22 | 100< | 15 |
| 40% acetone | 19 | 95 | 19 |
| 50% acetone | 26 | 80 | 21 |
| 60% acetone | 25 | 90 | 18 |

Results of the table 1 indicated that when 50% acetone aqueous solution was applied to extraction, a final product with a larger amount of polyphenol content exhibited the most potent inhibitory activity against glucosyltransferase.

REFERENCE EXAMPLE 2

Tests for Selecting the Optimum Extraction Temperature

The same procedure as described in Reference example 1 was performed except that the extraction process was repeated two times with 50% acetoneaqueous solution, solution, selected from Reference example 1, in the range of temperature as described in the following table 2. Further, tests for detecting the inhibitory activities of each extract against glucosyltransferase as well as for detecting polyphenol contents of each extract was performed in the same manner as Reference example 1, as shown in the following table 2.

TABLE 2

| Temperature (° C.) | Yield (%) | Inhibitory activity against Gtase | Contents of polyphenol (%) |
|---|---|---|---|
| 30 | 18.1 | 90 | 11 |
| 40 | 20.6 | 66 | 14 |
| 50 | 20.3 | 59 | 15 |
| 60 | 23.9 | 58 | 18 |
| 70 | 24.2 | 63 | 19 |
| 80 | 26.8 | 90 | 18 |
| 90 | 25.3 | 90 | 16 |

Results of the table 2 indicated that when the extraction process was performed in the presence of 50% acetone at 40~70° C. (preferably 60° C.), a final product with a larger amount of polyphenol exhibited the most potent inhibitory activity against glucosyltransferase.

REFERENCE EXAMPLE 3

Tests for selecting the optimum Extraction Time

The same procedure as described in Reference example 1 was performed except that the extraction process was performed in the presence of solvent (50% acetone aqueous solution), selected from Reference examples 1 and 2 at 60° C. for the range of time as described in the following table 3. Further, tests for detecting the inhibitory activities of each extract against glucosyltransferase as well as for detecting polyphenol contents of each extract was performed in the same manner as Reference example 1, as shown in the following table 3.

TABLE 3

| Extraction time | Yield (%) | Inhibitory activity against Gtase | Contents of polyphenol (%) |
|---|---|---|---|
| 1 hour | 20.6 | 65 | 13.7 |
| 2 hours | 21.3 | 60 | 14.0 |
| 3 hours | 23.9 | 60 | 13.8 |
| 4 hours | 25.5 | 57 | 14.0 |
| 5 hours | 25.4 | 59 | 13.6 |
| 6 hours | 24.8 | 60 | 13.8 |
| 7 hours | 23.8 | 67 | 13.4 |

Results of the table 3 indicated that when the extraction process was performed in the presence of 50% acetone aqueous solution at 60° C. for 4~6 hours, a final product with a larger amount of polyphenol exhibited the most potent inhibitory activity against glucosyltransferase.

Through the above mentioned Reference examples, the inventor et al. have found the optimum conditions for manufacturing the extract of cacao bean husk and detailed the optimum conditions based on the following examples. Hence, it is evident that this invention is not limited by the Examples.

COMPARATIVE EXAMPLE 1

300 ml of solvent, as described in the following table 1, was added to 30 g of well dried cacao bean husk (less than 2 mm in size), stirred at 60 rpm at 60° C. and extracted under reflux for 4 hours. After the extraction was completed, the solution was filtered off to collect the extraction solution only. Then, the same amount of 50% ethanol aqueous solution was added to the residue to perform the same extraction process repeatedly. The extraction solution, so obtained, is combined with the previously extracted solution, and concentrated by vacuum evaporator at 40~50° C. to obtain an extract of cacao bean husk.

Further, tests for detecting the inhibitory activities of each extract against glucosyltransferase as well as for detecting polyphenol contents of each extract was performed in the same manner as Reference example 1, as shown in the following table 5.

COMPARATIVE EXAMPLE 2

The currently marketed oolong tea extract (brandname: Sunoolong, Suntory Co. of Japan) was used for this study. Further, tests for detecting the inhibitory activities of each extract against glucosyltransferase as well as for detecting polyphenol contents of each extract was performed in the same manner as Reference example 1, as shown in the following table 5.

COMPARATIVE EXAMPLE 3

The currently marketed green tea extract (brandname: Tea polyphenol, manufacturer: T.Hasegawa Co., Japan). Further, tests for detecting the inhibitory activities of each extract against glucosyltransferase as well as for detecting polyphenol contents of each extract was performed in the same manner as Reference example 1, as shown in the following table 5.

EXAMPLE 1

An extract of cacao bean husk, so formed from Comparative example 1, was tested. 70 g of the extract was again added to a column (60×350 mm) containing the styrene-based adsorption resin for industrial use, washed with 1,400 ml of 20% ethanol solution at the elution rate of 50 ml/min. Then, 1,400 ml of 50% ethanol solution was again added to the resin at the elution rate of 50 ml/min and extracted by solvent to obtain a fraction of cacao bean husk with a tooth decay prevention function. Hence, 9 g of the fraction was recovered as a dry weight.

Further, tests for detecting the inhibitory activities of each extract against glucosyltransferase as well as for detecting polyphenol contents of each extract was performed in the same manner as Reference example 1, as shown in the following table 5.

EXAMPLES 2~9 AND COMPARATIVE EXAMPLES 1~6

A fraction of cacao bean husk was obtained in the same procedure as described in Example 1, except for using different reaction conditions such as extraction temperature and extraction time, as shown in the following table 4.

Furthur, tests for detecting the inhibitory activities of each extract against glucosyltransferase as well as for detecting polyphenol contents of each extract was performed in the same manner as Reference example 1, as shown in the following table 5.

TABLE 4

| Category | Extraction solvent | Extraction time | Extraction temperature |
|---|---|---|---|
| Example | | | |
| 1 | 50% acetone | 4 hours | 40 |
| 2 | 50% acetone | 4 hours | 50 |
| 3 | 50% acetone | 4 hours | 60 |
| 4 | 50% acetone | 5 hours | 40 |
| 5 | 50% acetone | 5 hours | 50 |
| 6 | 50% acetone | 5 hours | 60 |
| 7 | 50% acetone | 6 hours | 40 |
| 8 | 50% acetone | 6 hours | 50 |
| 9 | 50% acetone | 6 hours | 60 |
| Comparision example | | | |
| 1 | 50% methanol | 4 hours | 50 |
| 2 | 50% methanol | 1 hour | 50 |
| 3 | 50% methanol | 1 hour | 20 |
| 4 | 50% ethanol | 4 hours | 50 |
| 5 | 50% acetone | 4 hours | 90 |
| 6 | 50% acetone | 2 hours | 90 |

TABLE 5

| Category | | Inhibitory activity against Gtase as $IC_{50}$ ($\mu$g/ml) | Contents of polyphenol (%) |
|---|---|---|---|
| Comparison example | 1 | 60 | 13 |
| | 2 | 40 | 40 |
| | 3 | 250 | 40 |
| Example | 1 | 31 | 37 |
| | 2 | 26 | 37 |
| | 3 | 20 | 39 |
| | 4 | 30 | 38 |
| | 5 | 24 | 36 |
| | 6 | 20 | 38 |
| | 7 | 30 | 37 |

TABLE 5-continued

| Category | | Inhibitory activity against Gtase as $IC_{50}$ (μg/ml) | Contents of polyphenol (%) |
|---|---|---|---|
| | 8 | 21 | 36 |
| | 9 | 22 | 39 |
| Comparative example | 1 | 85 | 15 |
| | 2 | 90 | 15 |
| | 3 | 94 | 13 |
| | 4 | 81 | 18 |
| | 5 | 58 | 29 |
| | 6 | 55 | 25 |

Results of the table 5 showed that the fraction of cacao bean husk prepared according to this invention demonstrated about 2-fold inhibitory activity against cosyltransferase, compared with an extract of cacao bean husk obtained under solvent extraction (Comparative example 1), while maintaining very excellent inhibitory activity against glucosyltransferase, compared with the currently marketed Oolong tea extract (Comparative example 2) or green tea extract (Comparative example 3) as a tooth decay preventing agent.

As described above, this invention has some advantages in that a fraction of cacao bean husk, which has more potent activity against glucosyltransferase in the prevention of tooth decay, while providing an economically feasible recovery process designed to treat enormous wastes of cacao bean husk, is prepared by adsorption column chromatography in such a manner that the extract of cacao bean husk, so formed from cacao bean husk, is again added to an adsorption resin, and fractionated by 50% ethanol aqueous solution.

What is claimed is:

1. A process for manufacturing a fraction of cacao bean husk having more potent activity against glucosyltransferase in the prevention of tooth decay, comprising the steps of:
    a. extracting an extract of cacao bean husk by refluxing dried cacao bean husk in an aqueous acetone solution;
    b. adding the extract of cacao bean husk to a column containing a styrene-based adsorption resin;
    c. washing said extract of cacao bean husk with ethanol;
    d. fractionating said extract of cacao bean husk with ethanol;
    wherein, said process is an industrial-scale manufacturing process for treating said cacao bean husk.

2. A fraction of cocoa bean husk which is prepared according to claim 1, having a polyphenol concentration of 36–40% wherein said fraction of cacao bean husk is effective in preventing tooth decay.

3. The process for manufacturing a fraction of cacao bean husk according to claim 1 wherein the said extraction of an extract of cacao bean husk is carried out by refluxing dried cacao bean husk in 50% aqueous acetone solution at 40–70° C. for 4–6 hours.

4. The process for manufacturing a fraction of cacao bean husk according to claim 1, wherein the said extract of cacao bean husk is washed with 1–2 weight parts of 20% aqueous ethanol.

5. The process for manufacturing a fraction of cacao bean husk according to claim 1, wherein 1–2 weight parts of 50% aqueous ethanol is added to the washed extract of cacao bean husk for fractionation.

\* \* \* \* \*

UNITED STATES PATENT AND TRADEMARK OFFICE
CERTIFICATE OF CORRECTION

PATENT NO. : 6,159,451
DATED : December 12, 2000
INVENTOR(S) : Dong Young Kim et al.

It is certified that error appears in the above-identified patent and that said Letters Patent is hereby corrected as shown below:

Claim 2, column 10,
Line 15, change "cocoa" to read -- cacao --.

Claim 3, column 10,
Line 23, change "4-6hours" to read -- 4-6 hours --.

Signed and Sealed this

Twenty-third Day of October, 2001

Attest:

Attesting Officer

NICHOLAS P. GODICI
Acting Director of the United States Patent and Trademark Office